United States Patent [19]

Klaue et al.

[11] Patent Number: 5,002,544
[45] Date of Patent: Mar. 26, 1991

[54] OSTEOSYNTHETIC PRESSURE PLATE OSTEOSYNTHETIC COMPRESSION PLATE

[75] Inventors: Kaj Klaue, Spiegal, Hans Brunner, Waldenburg; Stephan M. Perren, Davos Dorf, all of Switzerland

[73] Assignee: Synthes (U.S.A.), Paoli, Pa.

[21] Appl. No.: 559,376

[22] Filed: Jul. 26, 1990

Related U.S. Application Data

[63] Continuation of Ser. No. 278,841, Dec. 2, 1988, abandoned.

[30] Foreign Application Priority Data

Dec. 2, 1987 [CH] Switzerland .................. 04710/87

[51] Int. Cl.⁵ .............................................. A61F 5/04
[52] U.S. Cl. ...................................... 606/69; 606/71
[58] Field of Search ..................................... 606/69–71, 606/105, 76, 77, 78, 101

[56] References Cited

U.S. PATENT DOCUMENTS

| | | |
|---|---|---|
| Re. 31,628 | 7/1984 | Allgower et al. |
| 247,357 | 9/1988 | Perren et al. |
| 2,486,303 | 10/1949 | Longfellow .................. 128/92 YP |
| 3,463,148 | 8/1969 | Treace .......................... 128/92 YP |
| 4,219,015 | 8/1980 | Steinemann ................. 128/92 YP |
| 4,429,690 | 2/1984 | Angelino-Pievani . |
| 4,493,317 | 1/1985 | Klave ........................... 128/92 YP |
| 4,503,848 | 3/1985 | Caspar et al. ................ 128/92 YP |
| 4,524,765 | 6/1985 | De Zbikowski .............. 128/92 YP |
| 4,683,878 | 8/1987 | Carter .......................... 128/92 YP |
| 4,781,183 | 11/1988 | Casey et al. ................. 128/92 YP |
| 4,838,252 | 6/1989 | Klaue .................................. 606/69 |

FOREIGN PATENT DOCUMENTS 451868  3/1948  Canada ......................... 128/92 YP

OTHER PUBLICATIONS

Ser. No. 247,357 filed 9/21/88, Perren et al.

Primary Examiner—Robert A. Hafer
Assistant Examiner—Michael Brown
Attorney, Agent, or Firm—Davis Hoxie Faithfull & Hapgood

[57] ABSTRACT

An osteosynthetic pressure plate having several holes for bone screws positioned along its longitudinal axis and having an underside with curved recesses, designed for positioning on the bone so that immediately upon implantation there are spaces between the bone and the pressure plate.

11 Claims, 4 Drawing Sheets und 5,002,544

OSTEOSYNTHETIC PRESSURE PLATE OSTEOSYNTHETIC COMPRESSION PLATE

This is a continuation of copending application Ser. No. 07/278,841 filed on Dec. 2, 1988, now abandoned.

FIELD OF THE INVENTION

The invention relates to an osteosynthetic pressure plate with several holes positioned along the longitudinal axis of the plate which are adapted to hold bone screws.

BACKGROUND OF THE INVENTION

Osteosynthetic pressure plates have been known for a long time, for example from Swiss Patent A5 462,375. Over the years, numerous improvements in pressure plates have been proposed. However, these improvements have been largely limited to the modification of individual construction features which have brought about gradual improvements but have not constituted any genuine innovative advance. Most pressure plates used in hospitals are therefore still of the conventional type.

U.S. Pat. No. 4,838,252, filed by one of us, K. Klaue, and assigned to the owner of the present invention, discloses osteosynthetic pressure plates having a reduced area of contact with the bone.

The pressure plate of the invention provides a significant advance through optimum selection of construction features which promote post-operative bone growth under the plate and guarantee a dynamic compression effect.

SUMMARY OF THE INVENTION

The invention provides an osteosynthetic pressure plate having an upper surface, a lower surface for application to a bone, a longitudinal axis and a plurality of screw holes positioned along the longitudinal axis, the cross section of the plate transverse to the longitudinal axis at at least one point being wider toward the upper surface than toward the lower surface and the plate having recesses in the lower surface so that upon application to a bone there is space between the bone and the plate. Plates according to the invention are preferably curved transversely to their longitudinal axes, so that their cross sections have the shape of the section of a cylinder. The cross section between the screw holes is reduced, preferably to the extent that the resistance of the plate to bending in this area is less than in the area of the holes. Because of the reduced bend resistance between the holes, the plate can more easily be adapted to conform to the anatomy of the bone. Furthermore, this can be done without deformation of the holes, thus minimizing the resulting loss of fatigue strength and minimizing the misfit of the screw heads.

For some purposes, it has proved advantageous to construct the pressure plate of the invention as a dynamic compression plate (according to U.S. Pat. No. Re 31,628) with at least one appropriately shaped hole.

The advantages of the invention are first, that the adaption of the pressure plate to the anatomy of the bone is easier to achieve; second, that vascularization and hence bone growth under the pressure plate are considerably improved; and third, that removal of the plate from a healed bone is facilitated.

DESCRIPTION OF THE DRAWINGS

The invention will be described more fully in connection with the accompanying drawings in which.

DETAILED DESCRIPTION

Figure 1:
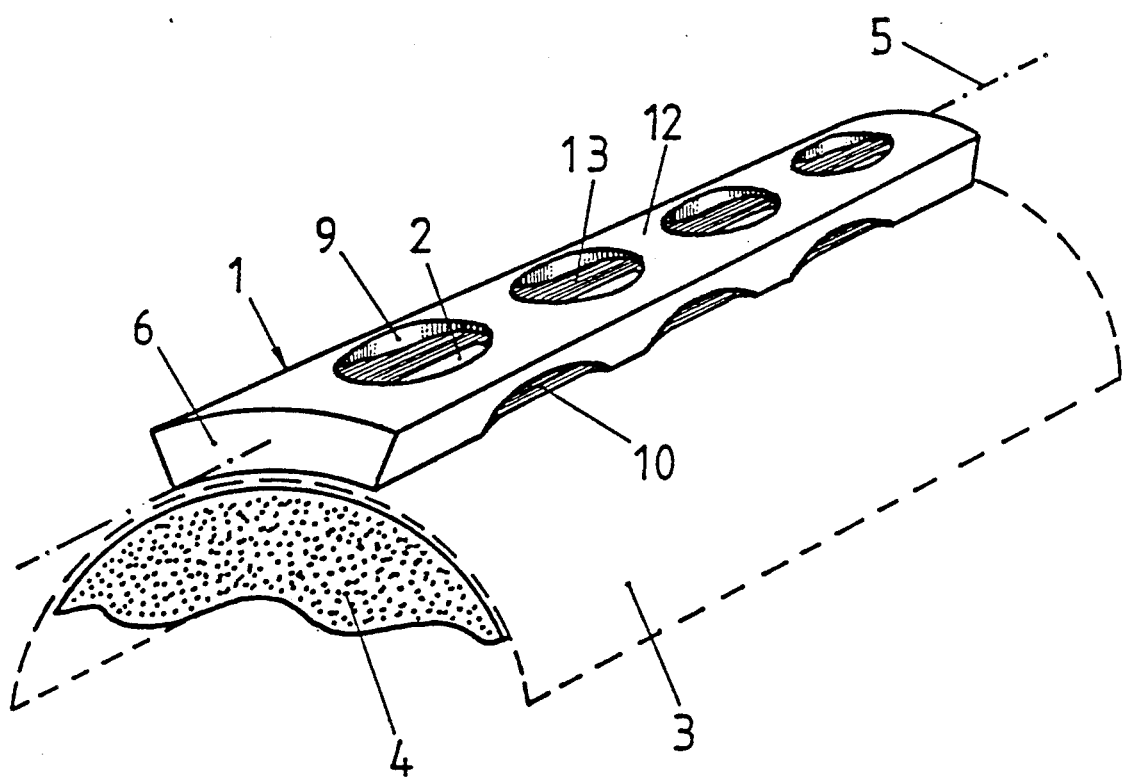
FIG. 1 is a perspective view of an osteosynthetic plate according to the invention.
Figure 2:
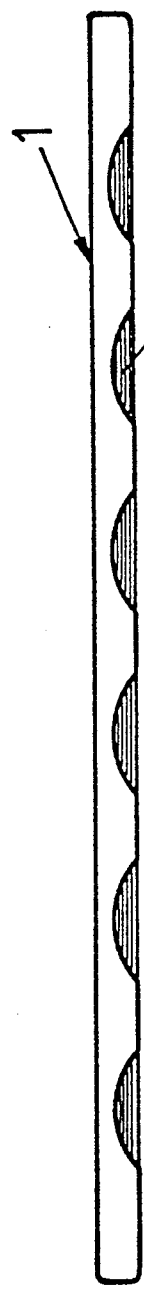
FIG. 2 is a view in side elevation of an osteosynthetic pressure plate according to the invention.
Figure 3:
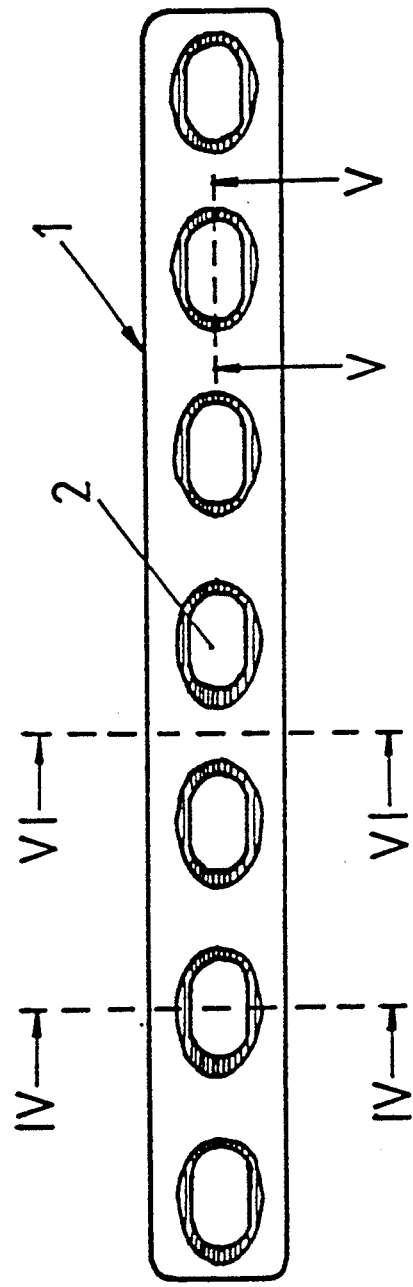
FIG. 3 is a plan view of an osteosynthetic pressure plate according to the invention.

As shown in FIGS. 1 to 3, the osteosynthetic pressure plate of the invention consists of an oblong pressure plate 1, which is curved transversely to its longitudinal axis 5, so as to have a cross section in the shape of a section of a hollow cylinder. Several holes 2 are positioned along the longitudinal axis 5 to hold screws for fastening the plate to a bone. These holes may be circular, but as shown in the drawing are preferably oblong; most preferably they are shaped interiorly to provide a camming function to achieve fracture reduction as described in U.S. Pat. No. Re 31,628.

The cross section 6 of the pressure plate 1 in a plane perpendicular to the longitudinal axis 5 is wider towards the upper surface 12 of the plate than towards the lower surface, i.e., that surface which will be placed next to the bone. The cross section has this shape at at least one point along the longitudinal axis 7. Moreover, the underside of the plate, intended for positioning on bone 4, has recesses 10 so that upon implantation there is space between the bone and the plate.

Figure 4:
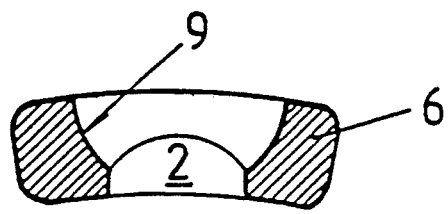
FIG. 4 is a cross section perpendicular to the longitudinal axis of the pressure plate along line IV—IV in FIG. 3.

The cross section 6 as shown in FIG. 4 is taken along line IV—IV of FIG. 3 through the center of a hole 2. As shown, the upper section of the hole has a spherical bearing surface 9, to receive the round head of a bone screw.

Figure 5:
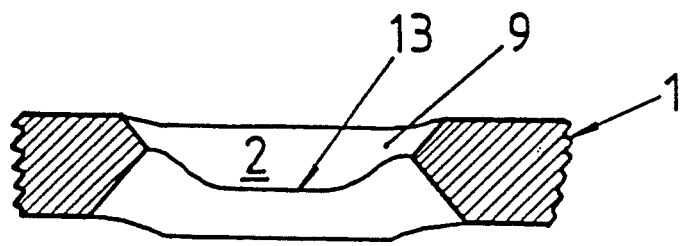
FIG. 5 is a cross section parallel to the longitudinal axis of the pressure plate along lines V—V in FIG. 3.

FIG. 5 shows a partial cross section in the plane of the longitudinal axis 5. The upper portion of hole 2 has bearing surface 9, which narrows and then opens out again towards the bone application surface in order to permit the insertion and gliding of inclined screws. The oblong hole 2, positioned symmetrically to longitudinal axis 5, has its side walls shaped to form an abutment 13 sunk opposite the top 12 of pressure plate 2. The abutment 13 may form a ramp upon which a screw head can slide in a direction parallel to longitudinal axis 5.

Figure 6:
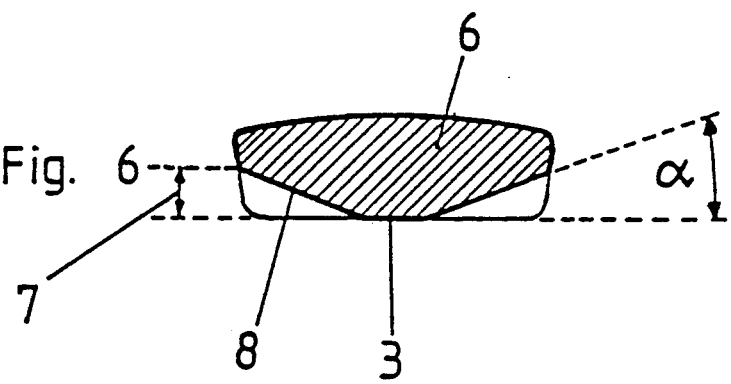
FIG. 6 is a cross section perpendicular to the longitudinal axis of the pressure plate along VI—VI in FIG. 3.

The cross section 6 shown in FIG. 6 taken between screw holes has an approximately trapezoidal shape. The recesses 10 are cut into the lower surface of the plate a distance shown as 7. As shown in FIG. 6, in one preferred embodiment of the invention, the element of the cut-out section 10, at its maximum distance from the lower surface 3, forms an angle, alpha, of about 20° with lower bone application surface 3. Depending on the area of application, this angle can vary within a range of 12°-28°, preferably within 18°-22°.

Figure 7:
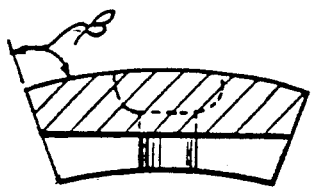
FIGS. 7 and 8 are cross sections taken between holes in another embodiment of the invention.
Figure 8:
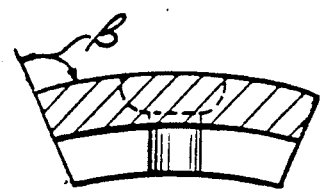

In the embodiments of FIGS. 7 and 8 the entire area between screw holes is cut away so that there is no plate-bone contact. The plate may be curved, as shown, and the side walls of the plate are preferably inclined inwardly toward the bone. In general the larger the angle beta, as shown in FIGS. 7 and 8, the more satisfactory the bone growth around the plate.

Figure 9:
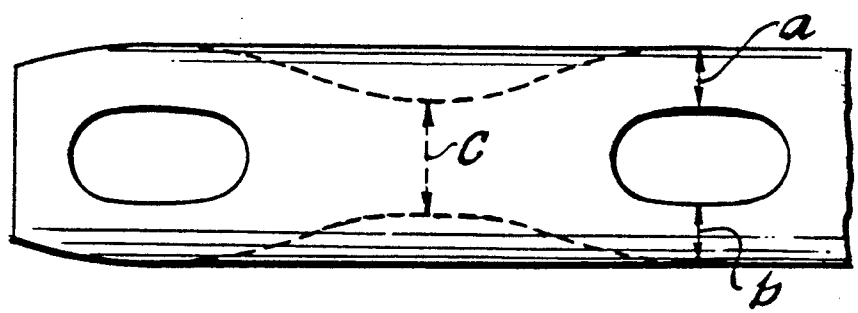
FIG. 9 is a plan view of a plate made according to still another embodiment of the invention in which the area of the plate in contact with the bone is approximately the same at the holes and between the holes.
Figure 10:
FIG. 10 is a plan view of a plate according to another embodiment of the invention in which the area of contact at the holes and between the holes approaches zero.
Figure 10:
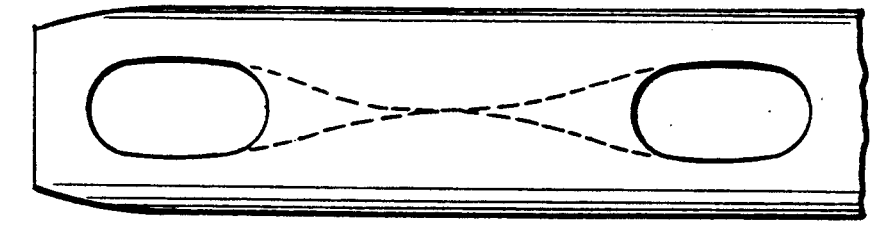
Figure 11:
FIGS. 11 and 12 are cross sections of the plate of FIG. 10 at XI—XI and XII—XII.
Figure 11:
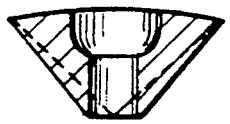
Figure 12:
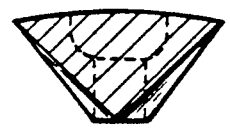

In FIGS. 9-12 there are shown plates in which the area of contact between plate and bone is approximately the same in the region of the holes and between the holes. Referring to FIG. 9, the transverse distances a and b between the hole and the side wall of the plate at the bone are equal to the transverse distance c which is between the holes. In other words, the effective width (a plus b; or c) of the lower surface of the plate is constant. These distances can be made quite small, for instance, less than 4 mm or preferably less than 2 mm. In FIGS. 10, 11 and 12 the distances a, b, and c of FIG. 9 are reduced to essentially zero and the locus of bone-plate contact becomes a line.

A wide range of other inter-hole cross sections are possible, all having in common the reduction of the area of the plate brought in contact with the bone, compared to that of conventional pressure plates, as well as a decreased bending yield strength between the holes. In a further embodiment of the invention, not shown, the underside 3 of the plate is convex instead of concave, for example, having a ellipsoid, paraboloid or other similar shape. In these embodiments, contact with the bone is essentially reduced to a line, which permits a reliable splinting effect.

Improved clinical results have been achieved with plates according to the invention. Best fit of the plate to the shape of the bone is due to the plate's modified bending resistance. The plate's configuration also causes minimal bone contact, which in turn promotes vascularization and bone growth.

An additional advantage is that the plate is easier than conventional plates to remove from the healed bone. When a compression plate is placed on a bone, new bone growth fills in around the corner of the lower outer edge of the plate. This bony plate embedment, called the plate bed, is formed as a reaction by the bone to the presence of the implanted plate. The plate bed formed by conventional pressure plates has sharp edges. Surprisingly, it has been found that after removal of an implanted pressure plate according to the invention, the plate bed has rounded edges, making it easier to remove the plate after the broken bone has healed, without the use of instruments and without destruction of the newly formed bone lamellae of the plate bed. The undamaged bone lamellae strengthen the bone cross section in the area of the fracture, and thereby reduce the danger of another fracture.

Further advantage found is the eased bending and torsion of the plate, previous to application, and known as "adaptation" of the plate.

What is claimed is:

1. An osteosynthetic compression plate having a central longitudinal axis, an upper surface with two side edges generally parallel to the central axis, a lower surface for application to a bone, and a plurality of screw holes along the central axis, the edges of said upper surface being more remote from said central axis in a direction perpendicular to said central axis, than any other part of said plate, said plate having recesses in its lower surface extending both parallel to and transverse to the central axis to provide space between the lower surface of the plate and the bone.

2. An osteosynthetic compression plate as claimed in claim 1 wherein the cross section is in the shape of a section of a cylinder.

3. An osteosynthetic compression plate as claimed in claim 1 wherein the pressure plate has an oblong screw hole with its long sides in the same direction as the longitudinal axis of the plate, said hole having side walls adapted to form an abutment for a screw head, enabling a screw head to slide parallel to the longitudinal axis of the plate.

4. An osteosynthetic compression pressure plate according to claim 1, wherein the recesses form an angle of about 12° to about 28° with the lower surface in the area between the screw holes.

5. An osteosynthetic compression pressure plate according to claim 4 wherein the angle is in the range of about 18° to about 22°.

6. An osteosynthetic compression pressure plate according to claim 1, wherein the upper portion of at least one hole is constructed as a spherical surface for receiving a screw head.

7. An osteosynthetic compression pressure plate according to claim 1, wherein the cross section profile has an approximately trapezoidal shape at one point along the longitudinal axis.

8. An osteosynthetic compression plate according to claim 1, wherein, on the lower surface of the plate, the width of the inter-hole areas and the sum of the widths of the two areas between the sides of each hole and the corresponding side of the plate, are equal and constant over the length of the plate.

9. An osteosynthetic compression pressure plate according to claim 8, wherein the width of the interhole area of the undersurface of the plate for contact with a bone is less than 4 mm.

10. The plate claimed in claim 8 wherein the width of the interhole area is less than 2 mm.

11. An osteosynthetic compression plate having an upper surface, a lower surface for application to a bone, a longitudinal axis, and a plurality of screw holes positioned along the longitudinal axis, the cross section of the plate transverse to the longitudinal axis at least at one point on said axis being wider toward the upper surface than toward the lower surface and said plate having recesses in the lower surface so that upon application to a bone there is space between the bone and the plate, wherein the area of the cross section is reduced between screw holes so that the bending resistance of the plate in the sections between holes is no greater than in the sections where holes are located.

* * * * *